US 6,633,159 B1

(12) United States Patent
Robar et al.

(10) Patent No.: US 6,633,159 B1
(45) Date of Patent: Oct. 14, 2003

(54) METHOD AND APPARATUS FOR MAGNETIC DETECTION OF DEGRADATION OF JACKETED ELEVATOR ROPE

(75) Inventors: Terry M. Robar, Canton, CT (US); William A. Veronesi, Hartford, CT (US); Paul A. Stucky, Groton, CT (US); Jack F. Gieras, Glastonbury, CT (US)

(73) Assignee: Otis Elevator Company, Farmington, CT (US)

( * ) Notice: Subject to any disclaimer, the term of this patent is extended or adjusted under 35 U.S.C. 154(b) by 0 days.

(21) Appl. No.: 09/280,637

(22) Filed: Mar. 29, 1999

(51) Int. Cl.$^7$ .......................... G01N 27/82; G01R 33/12
(52) U.S. Cl. ...................... 324/240; 324/235; 324/239; 324/242; 187/391
(58) Field of Search ................................. 324/235, 239, 324/240, 241, 242, 243, 226; 187/391, 373, 394

(56) References Cited

U.S. PATENT DOCUMENTS

| 4,096,437 A | | 6/1978 | Kitzinger et al. ........... 324/227 |
| 4,270,088 A | | 5/1981 | Weischedel ................... 324/241 |
| 4,427,940 A | * | 1/1984 | Hirama et al. ............... 324/240 |
| 4,439,731 A | * | 3/1984 | Harrison ...................... 324/239 |
| 4,538,107 A | * | 8/1985 | Varone ......................... 324/242 |
| 4,659,991 A | | 4/1987 | Weischedel .................. 324/241 |
| 4,827,215 A | | 5/1989 | Van der Walt ............... 324/227 |
| 4,864,233 A | * | 9/1989 | Harrison ...................... 324/240 |
| 4,929,897 A | | 5/1990 | Van Der Walt .............. 324/240 |
| 5,036,277 A | | 7/1991 | Van der Walt ............... 324/235 |
| 5,198,765 A | | 3/1993 | Van Der Walt .............. 324/227 |
| 5,321,356 A | | 6/1994 | Weischedel .................. 324/227 |
| 5,402,066 A | | 3/1995 | Hickman, Jr. et al. ....... 324/242 |
| 5,414,353 A | | 5/1995 | Weischedel .................. 324/232 |
| 5,426,362 A | * | 6/1995 | Ninnis .......................... 324/235 |
| 5,453,291 A | * | 9/1995 | Sasahara et al. ............. 324/240 |
| 5,565,771 A | | 10/1996 | Hamelin et al. ............. 324/225 |
| 5,570,017 A | | 10/1996 | Blum ........................... 324/232 |
| 5,751,144 A | | 5/1998 | Weischedel .................. 324/240 |
| 5,804,964 A | | 9/1998 | Hamelin et al. ............. 324/242 |
| 6,133,731 A | * | 10/2000 | Melamud et al. ............ 324/209 |

FOREIGN PATENT DOCUMENTS

| DE | 3 904 612 A1 | 3/1990 |
| EP | 0286712 | 6/1987 |
| EP | 0 286 712 A2 | 10/1988 |
| EP | 0816797 | 6/1997 |
| EP | 0 845 672 A1 | 6/1998 |

OTHER PUBLICATIONS

English translation of DE 39 04 612 A1.

* cited by examiner

Primary Examiner—Walter E. Snow

(57) ABSTRACT

A method and system for detecting or measuring defects in a rope having ferromagnetic tension members includes a magnetic field exciter and an array of magnetic flux sensors corresponding to the tension members in a known relationship. Measurements of magnetic flux leakage are indicative of defects. Another aspect of the invention includes a method and system for detecting or measuring defects in an elevator rope having electrically conductive tension members, whereby measured electrical resistance in the tension members is indicative of defects.

5 Claims, 5 Drawing Sheets

METHOD AND APPARATUS FOR MAGNETIC DETECTION OF DEGRADATION OF JACKETED ELEVATOR ROPE

TECHNICAL FIELD

The present invention relates to elevator ropes and, more particularly, to a method and apparatus for testing elevator ropes to detect degradation using electrical or magnetic energy.

BACKGROUND OF THE INVENTION

Tension rope systems for lifting elevator cars, or similar vessels for vertically raising and lowering loads in industrial or commercial applications, are typically made up of steel ropes. Such ropes typically comprise multiple cords which, in turn, generally comprise a plurality of strands that are made up of individual steel wires. Such tension ropes are critical components upon which safety and productivity often depend.

Deterioration of individual components of a multi-strand or multi-cord rope adversely affects tension strength of the rope. The tension strength of a rope is dependent upon various parameters including its cross-sectional area. When one or more components of a steel rope stretch, tear or permanently bend, those components are disabled or weakened as load bearing members and, thus, the effective tension-bearing cross-sectional area of the rope is reduced. This type of deterioration can occur through a variety of ways, such as normal wear and tear, impact, fatigue or inadvertent corrosion.

Because service ropes, such as elevator ropes, are very long and are made up of many individual wires and strands, it is impractical to perform thorough and accurate testing of rope condition or deterioration level simply by visual inspection. Furthermore, it is impractical to disassemble elevator ropes and apply them to various testing devices. Thus, it is common in the industry to substantially overdesign the ropes to allow for a large margin of deterioration without a large risk of failure. The ropes are replaced at time or cycle milestones. Occasional in-field visual inspections are typically the only means of testing.

The main problem with visual inspection of ropes is that the eye can only see the strands and wires on the outer surface of the rope, which make up only a fraction of the tension-bearing cross-sectional area. Also, it is difficult to visually inspect an entire length of rope installed in, for example, an elevator system. Thus, sampling and approximation methods are generally employed. These methods still require a large margin of overdesign to ensure safety. As a result, ropes are designed with excessive and costly materials, and ropes are often discarded well before their useful life expires. In addition, man hours and operation down-time for inspection are often costly.

OBJECTS AND SUMMARY OF THE INVENTION

Various objects of the present invention include providing a method and apparatus for detecting deterioration of steel ropes or compound ropes having steel ropes as members, wherein detection is practical in time, cost and complexity, wherein continuous monitoring and detection are practical and efficient, and further wherein detection is accurate and reliable. Another object achieved is the ability to inspect rope components that are not viewable, such as in the case of compound ropes or belts including flat ropes in which one or more steel ropes are embedded in an insulator, such as polyurethane or rubber. In this situation, visual inspection is impossible. These and other objects are achieved by the present invention as described below.

One embodiment of the present invention involves applying a novel arrangement of magnets and sensors for saturating magnetically permeable ropes with a magnetic field and then obtaining magnetic flux leakage measurements for comparison to pre-stored data in order to determine rope condition. Another embodiment of the present invention involves applying electric current to a rope and measuring resistance values for comparison to pre-stored data in order to determine rope condition.

While the preferred embodiments are described below with respect to elevator ropes, by way of example, it is acknowledged that the present invention has application to other types of ropes and belts subject to similar loading and use conditions.

DESCRIPTION OF THE PREFERRED EMBODIMENTS

Magnetic Flux Method and Apparatus

A defect such as a crack, cut or other discontinuity in a ferromagnetic member, such as a wire, can be detected by monitoring magnetic flux density distribution within. A defect will result in penetration of the magnetic flux to the air. The quantitative determination of loss of metallic cross-sectional area, in a rope having wires of a diameter of 0.175 mm, caused by deterioration or defect is possible with quantitative resolutions of 0.175 mm. The terms "quantitative resolution" as used herein refers to the required minimum flaw for which the sensor provides a quantitative measure directly, without additional signal processing.

The most prevalent modes of deterioration of wire ropes include internal abrasion, corrosion, breaking and kinking. Internal abrasion is caused by nicking, high pressure or poor lubrication. Corrosion, which can occur internally or externally, is caused by various environmental conditions and poor lubrication. Breaking of wires results from fatigue, plastic wear, martensitic brittling, and mechanical damage. Kinking results from sharp bending or mechanical damage.

Deterioration results in loss of cross-sectional area of wires which reduces tension load bearing capacity. The transfer of load from a defective or deteriorated wire to neighboring wires will reduce the expected fatigue life of the remaining wires. As the number of defects in a group increases, the rate of increase in number of defects will accelerate due to increasingly displaced loads.

A system for detection of the leakage flux basically consists of a magnetic flux exciter and a magnetic flux sensor. The exciter is necessary to magnetize the ferromagnetic part to be inspected. It can be in the form of, for example, an encircling coil, or a U-shaped electromagnet or permanent magnet with mild steel poles. Encircling coils do not have ferromagnetic cores and, thus, result in poor utilization of the produced magnetic flux to magnetize the part being tested. U-shaped magnets are better because the can direct most of the produced magnetizing flux to the part being tested. Permanent magnet exciters do not require any power supply and they are smaller than electromagnets producing the same flux. Various magnetic flux sensors are available such as, for example, search coils, Hall elements, and magnetodiodes. Search coils allow for inspection of large surface areas but, however, their output signal is speed dependent. Hall elements can produce high output signals which are independent of speed.

Figure 1:
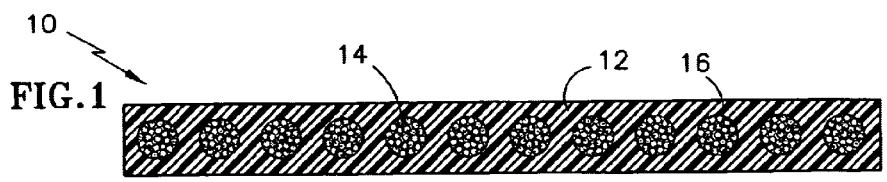
FIG. 1 is a schematic, cross-sectional view of an elevator rope having multiple cords in an insulator material.
Figure 2:
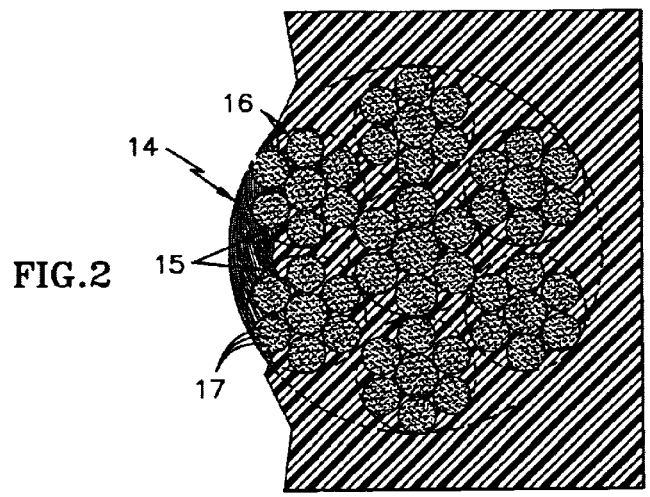
FIG. 2 is a schematic, cross-sectional view of a cord of an elevator rope of the type illustrated in FIG. 1.

Applying the exciter-sensor system to a flat rope made up of a series of wire cords is described with respect to FIG. 1–6. While the preferred embodiment is described in the context of a flat rope of non-ferromagnetic insulator material having ferromagnetic cords cords embedded therein, the invention is not limited to such an embodiment and may be applied to, for example, a compound rope having a single ferromagnetic cord embedded in a round insulator jacket. A flat rope (10) has a generally rectangular cross-sectional area of non-ferromagnetic insulator material , such as polyurethane, (12) surrounding a plurality of generally uniformly distributed steel ropes (14), each consisting of a plurality of cords (15). As illustrated in FIG. 2, a cord (15) comprises a plurality of strands (16). Each strand (16) is made up of a plurality of steel wires (17). In order to apply the magnetic flux exciter-sensor system according to the present invention, the following presumptions are made: (a) leakage fluxes are negligible; (b) magnetic permeability of the ferromagnetic poles and yokes of the exciter tends to infinity; and (c) no eddy currents are induced in the tested strands.

Figure 3:
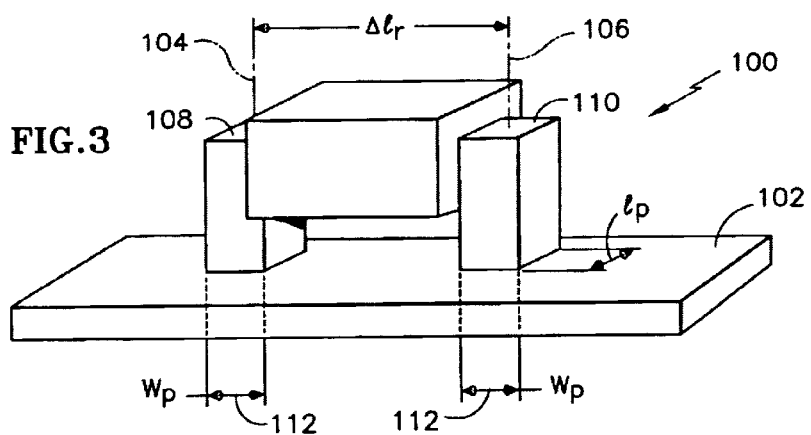
FIG. 3 is schematic diagram of a two magnets arranged adjacent to a ferromagnetic member.

Referring to FIG. 3, a schematic illustration shows a permanent magnet (100) positioned adjacent to a ferromagnetic test sample (102) representing the rope (10). The reluctance $R_{\mu r}$ of the steel ropes (14) is $$R_{\mu r} = \frac{\Delta l_r}{\mu_o \mu_n S_r},$$

where $\Delta_r$ is the tested segment of the cord equal to the distance between center lines of poles of the exciter.

The magnetic permeability of free space, $\mu_o$, is $\mu_o = 0.4\pi \times 10^{-6}$ H/m.

The relative magnetic permeability of steel strands is $\mu_r$. The cross-section are of the steel wire rope (14) is $S_r$. The magnetic permeability $\mu_{rr}$ is a nonlinear function of the magnetic flux density in strands (magnetic field intensity).

The cross section area $S_r$ of the steel rope (all steel strands) is $$S_r = n_c n_{str} \frac{\pi d_{str}^2}{4},$$

wheren $n_c$ is the number of strands, $n_{str}$ is the number of strands in each cord and $d_{str}$ is the diameter of a single strand.

The reluctance $R_{\mu g}$ of the airgap between pole faces and cores is, approximately, $$R_{\mu g} = \frac{g}{\mu_o S_g},$$

where g is the airgap (ferromagnetic body to ferromagnetic body) and $S=\omega p l_p$. The width of the pole face (parallel to the rope length) is $\omega_p$ and the length of the pole face (transverse to the rope length) is $l_p$.

According to Ohm's Law for magnetic circuits and including assumptions (a), (b) and (c) as stated above, the magnetic flux produced by the excitation system (with electromagnet or permanent magnet) is $$\Phi = \frac{NI}{\frac{\Delta l_r}{\mu_o \mu_r S_r} + \frac{2g}{\mu_o S_g}}$$

and the magnetic flux density in the rope (equal to the magnetic flux density in a single strand) is $$B = \frac{\Phi}{S_r} = \frac{\mu_o NI}{\frac{\Delta l_r}{\mu_r} + \frac{2g S_r}{S_g}}$$

where N is the number of turns of the electromagnet winding used for the excitation and I is the d.c. current in the electromagnet winding. The equivalent magnetic motive force (MMF) NI can also be produced by a permanent magnet. For a permanent magnet NI should be replaced by $Hh_M$ where H is the equivalent magnetic field intensity and $h_M$ is the length of the permanent magnet.

Using Hall elements, a system's sensitivity can be configured sufficiently to enable detection of a difference in magnetic flux density representative of the loss of one wire having a diamter of, for example, 0.175 mm in a cord of diameter 1.6 mm. By sampling rope as it deteriorates, determining magnetic flux density, and storing the measurement, data can be'stored for comparison to magnetic flux density for a rope to be tested. Using Hall elements, a system can be configured sufficiently to enable detection of a difference in magnetic flux density between the non-deteriorated rope and a test subject in which only one wire is broken.

To provide the level of sensitivity needed to detect differences in magnetic flux density of individual wires at such dimensions, the magnetic flux excitation system, comprising a U-shaped electromagnet or permanent magnet, should be configured using a small distance, $\Delta l_r$, between the centerlines (104, 106) of mild steel poles (108, 110). If $\Delta l_r$ is too small, however, the leakage flux can reduce the useful flux in the steel rope to an unacceptable level. The cross section area of each airgap, approximately equal to the cross section area of each mild steel pole, should be small. This can be achieved by minimizing the width (112) of each pole face to a value not less than the diameter of a single cord of the rope. If the cross section area of the air gap is too small, a large leakage flux from pole-to-pole will occur.

The magnetic flux exciter-sensor system according to the present invention requires the test sample, an elevator rope having internal steel cords, for example, to be passed over the poles of a magnet so that at any instant the portions of the cords that are over and in between the poles are magnetized, becoming part of the magnetic circuit, and a magnetic flux density is established in the cords parallel to their axes. In an ideal, non-deteriorated rope the majority of magnetic flux is parallel to the rope. A deterioration defect, as described above, in a steel cord or wire thereof causes local fringing in the magnetic flux density, so that it forms a "bump" or discontinuity in the parallel direction of the flux. At the location of the defect there is some magnetic flux density directed in a direction normal to the axis of the cord. This normal flux density is what is detected as indicative of a defect in the rope by the system of the present invention.

The magnetic flux sensor assembly may include either Hall effect sensors, search coils, or other known sensors. By way of example, an arrangement employing Hall effect sensors is described with respect to the schematic, cross section illustration of FIG. 4. The sensor assembly (300) illustrated is for use with a rope (302) having twelve steel rope cords (304) evenly spaced therein and running parallel to the longitudinal axis of the rope (302). First and second banks (306, 308) of Hall effect sensors (310) are positioned above and below, respectively, the flat belt (306) to be tested so that the Hall effect sensors (310) correspond to individual cords (304). A single bank of sensors on only one side of the belt may be used. Any number of sensors may be used, as the number of sensors does not necessarily have to correspond to the number of cords. The sensor banks (306, 308) should be generally centered in a direction along the longitudinal axis of the flat rope (302) with respect to the poles of the magnet, since the components of magnetic flux density normal to the belt axis is at a minimum, midway between the poles. Thus, the detection of a significant normal flux at this location would indicate a defect in the steel cord.

Figure 4:
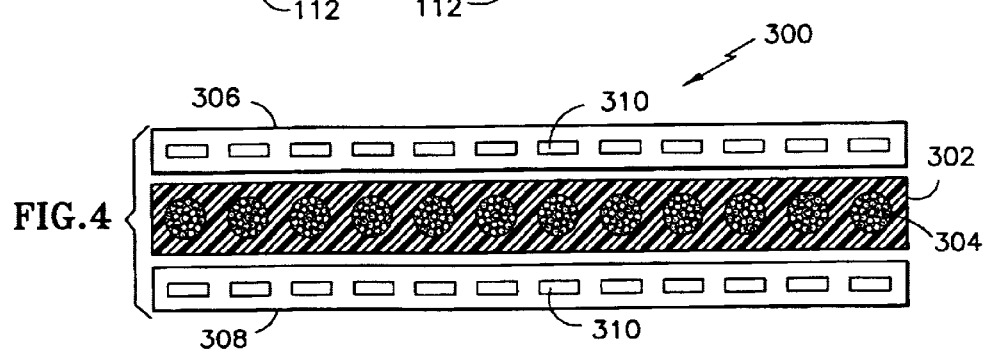
FIG. 4 is a schematic diagram of a magnetic flux sensor array adjacent to an elevator rope of the type disclosed in FIG. 1.
Figure 5:
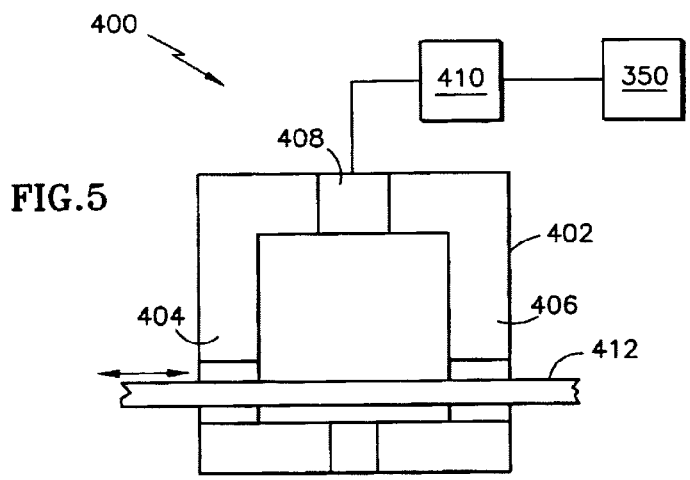
FIG. 5 is a schematic diagram of a first embodiment apparatus according to the present invention.
Figure 6:
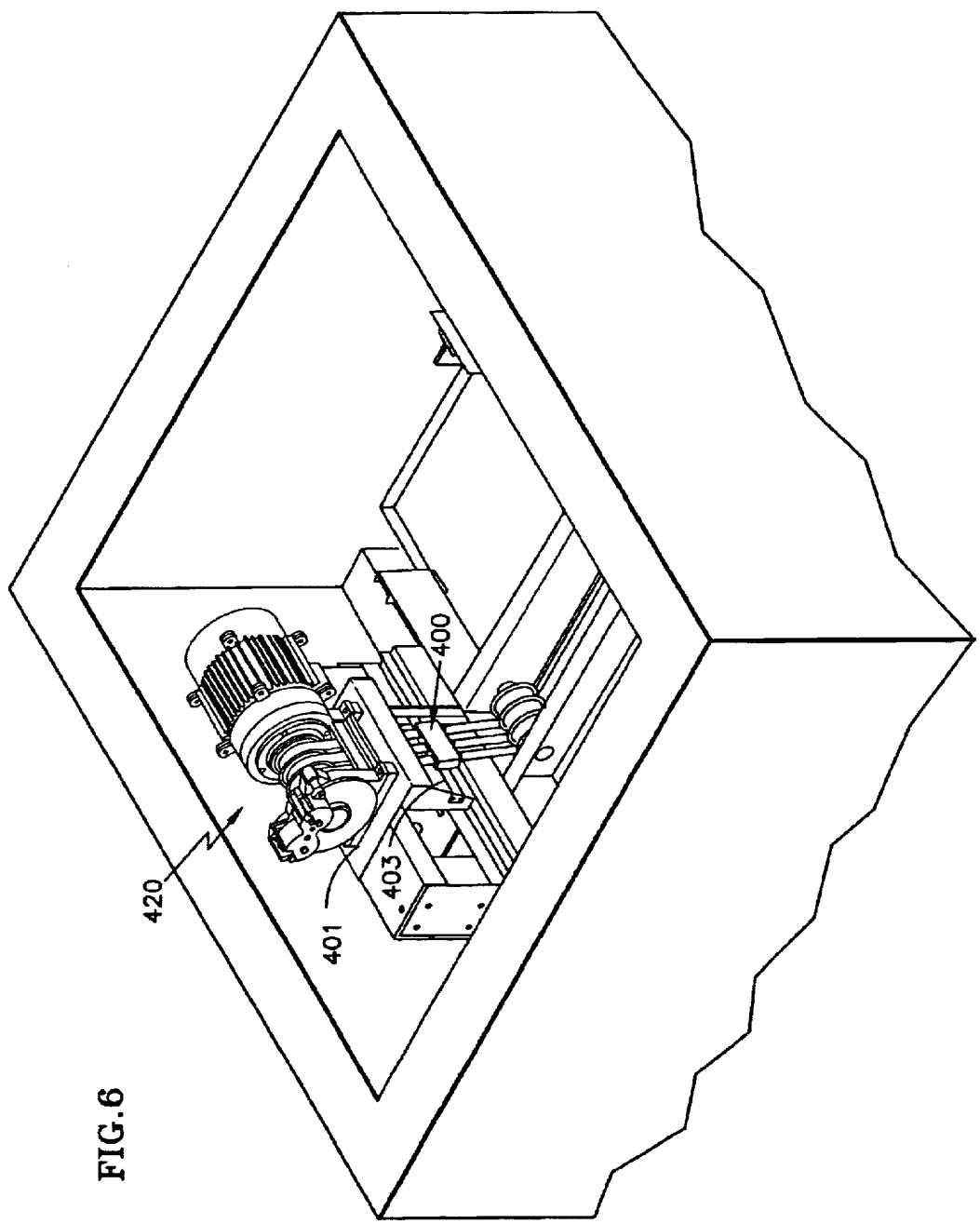
FIG. 6 is a partial, schematic view of a first embodiment apparatus according to the present invention mounted to an elevator system.

The testing assembly (400), shown schematically in FIG. 5, comprises an exciter system (402) having a U-shaped magnet with two poles (404, 406), a sensor assembly (408), as previously described with respect to FIG. 4, and a controller (410). The testing assembly (400) may be fixed as a dedicated unit to an elevator system (420), as shown in FIG. 6, or it may be assembled on-site and transportable to and from various sites. For example, the testing assembly (400) may be fixed to an elevator hoist machine assembly (401) by means of a bracket (403). The exciter and sensor assemblies are positioned so that a rope (412) to be tested may move relative to the magnet (402) and sensors (408). If desired, the controller (410) may be remotely located from the rest of the testing assembly (400) and in communication therewith through such means as hard-wire, RF, or modem. Remote monitoring and remote controlling may be implemented.

Figure 7:
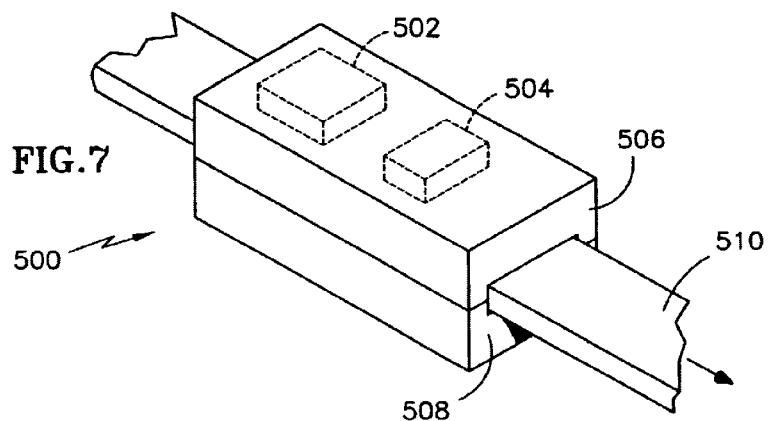
FIG. 7 is a schematic diagram of a second embodiment apparatus according to the present invention.

Alternatively, as shown in FIG. 7, the testing assembly (500) may be a self-contained, portable unit having an on-board controller (502) and power source (504) in addition to the components described with respect to FIG. 5. The unit may, for example, have a two-part housing comprising of halves (506, 508) which may be closed around an elevator rope (510) for testing.

A testing assembly designed for an array of cords (304) positioned in pre-determined relative positions within a rope (302) may be calibrated by first running a deteriorated rope sample, of known characteristics, through the testing assembly and pre-storing data signals from each individual Hall effect sensor. By relating each specific location for individual sensor elements, and repeating test runs with selectively damaged cords or strands, actual test data can be compared to known or predictable pre-stored data. By analyzing, for example, measurements from several sensor elements as they relate to only one rope at a known location, precise levels of defective strands or wires and their relative position within the cord cross section can be determined.

Figure 8A:
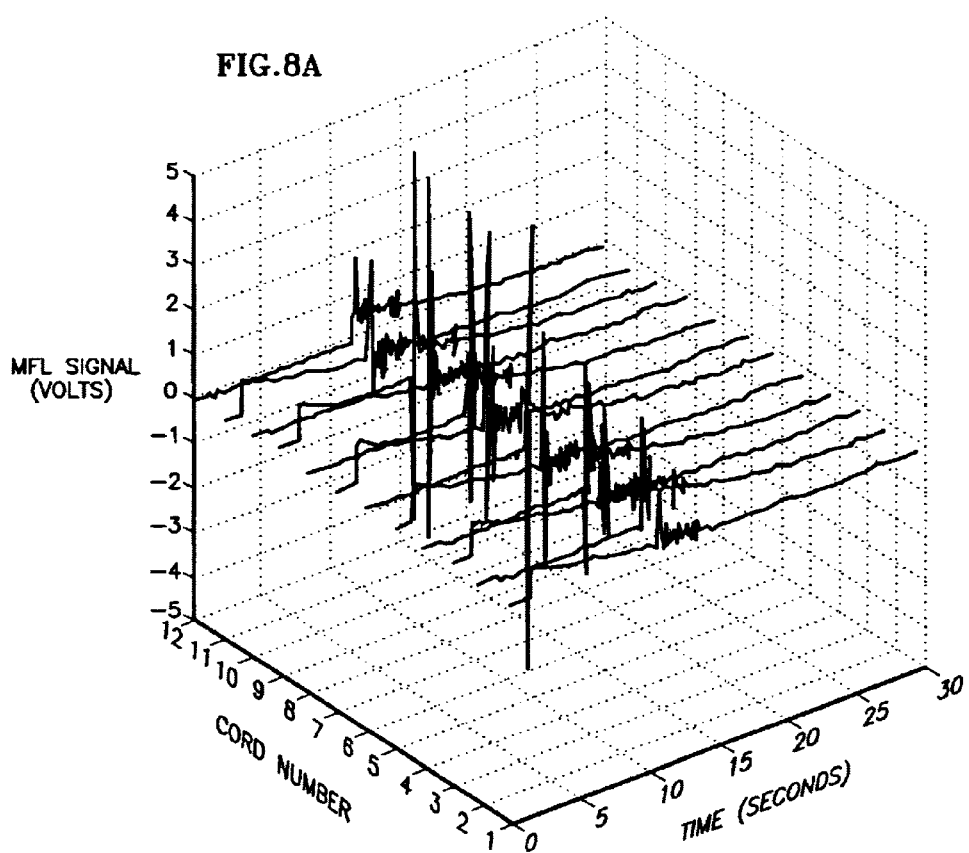
FIGS. 8A–8B are graphs illustrating magnetic flux detection according to the present invention.

By way of example, the graph shown in FIG. 8A depicts magnetic flux leakage for each cord of a flat, multi-cord rope under tension as a function of time measured by a bank of top-side sensors. For each cord, identified by cord number, the magnetic flux leakage in volts is plotted against time in seconds. The relative peaks on the magnetic flux leakage axis identify defects. Because the starting position on the rope and the rate of movement of the rope relative to the sensors is known, the time axis can be correlated to location on the rope. A similar graph for bottom-side sensors is provided in FIG. 8B. The graphs in 8A and 8B are complementary with respect to longitudinal position along the rope and depict the same period in time for the same rope. The output for the two sets of sensors (FIG. 8A and FIG. 8B) differs because of precise locations of defects. More precisely, the location of a defect on each cord can be located with respect to angular position and distance from the central axis of the cord, in addition to longitudinal position, by correlating reference points between the two sensor arrays.

Figure 8B:
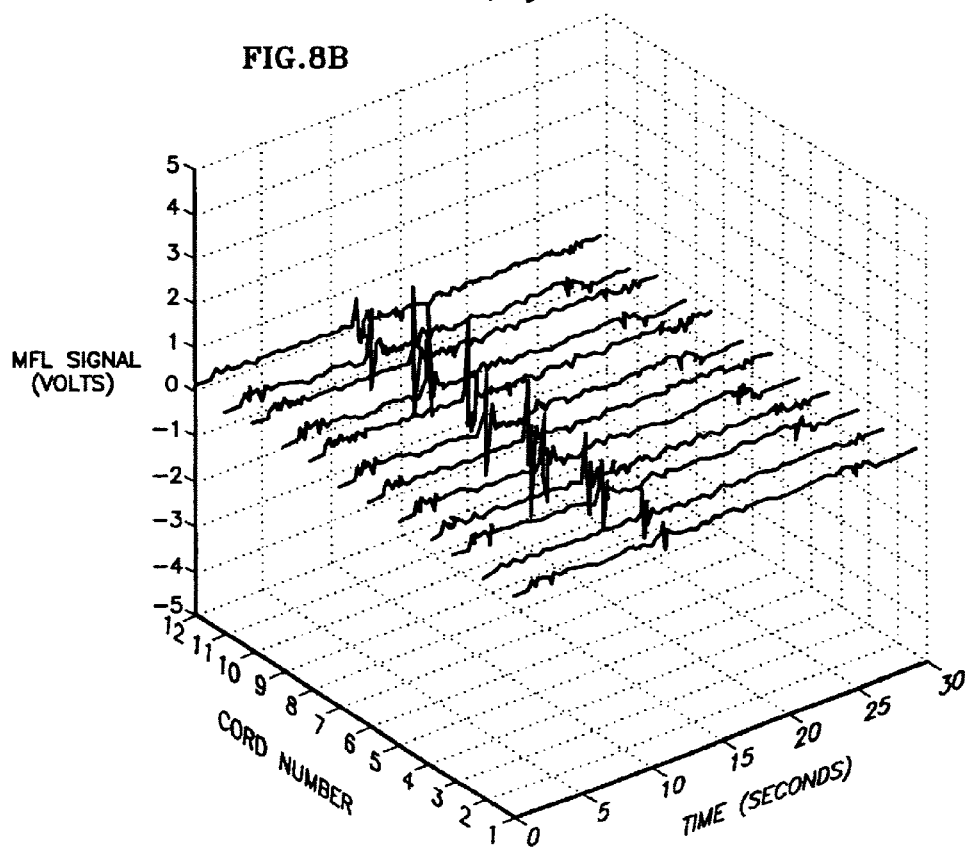

The above example described in FIGS. 8A and 8B is one example of various tests that can be used to precisely measure or locate wire or cord performance or failure under various conditions.

This approach, with this level of resolution, enables precise detection of wire or rope failure. Such measurements are useful, for example, for identifying chronic failure or wear patterns that may be indicative of problems with surrounding hardware or environment.

Electrical Resistance Measurement Method and Apparatus

Another embodiment of the present invention relates to detecting deterioration of steel cord tension load carrying members that are encased in non-condutive insulator materials, such as a flat rope constructed of, for example, polyurethane, by directing electric current through the steel cords and measuring electrical resistivity. An example of such a rope is a flat elevator rope having a polyurethane jacket with tension load carrying cords encased within and running the length of the rope. Changes in the resistivity of a steel rope are indicative of defective strands or wires. In the elevator environment, such testing requiring conductance is not possible with non-insulated belts or ropes where steel cords come into contact with metallic components of the elevator system.

According to the present invention, an electrical resistance measuring device is applied to a rope to be tested so that measured resistance through the cord can be correlated to pre-stored test data for an ideal rope. Predetermined threshold data values are used to determine when a tested rope or belt should be replaced. The resistance measuring device maybe, for example, a Kelvin bridge.

Figure 9:
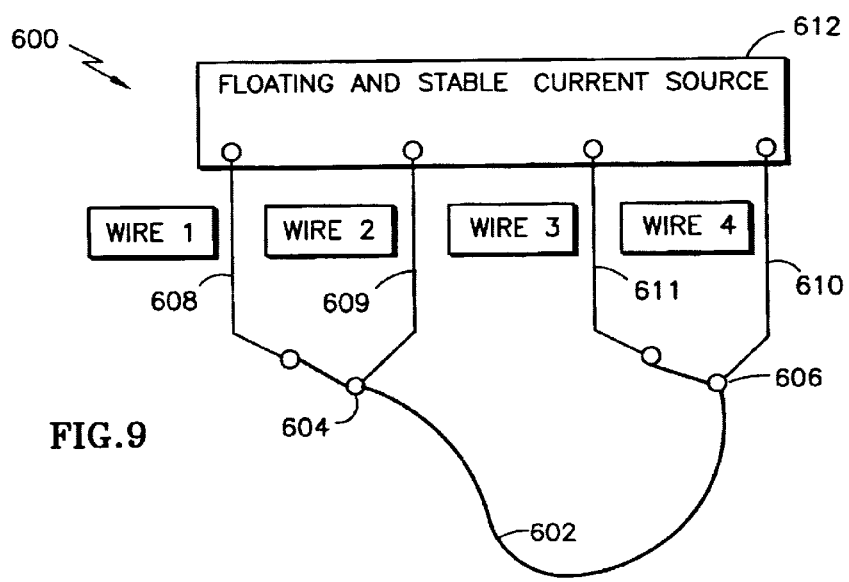
FIG. 9 is a schematic diagram illustrating a third embodiment of the present invention.

A schematic representation of such a system (600) is shown in FIG. 9, where an elevator rope (602) is connected at first and second ends (604, 606) to current input and output leads (608, 610). A floating stable constant current source (612) is supplied at one end of the rope (602). Connections are made at both ends and the voltage is measured. The measuring current is passed through the unknown resistance of the rope through the input wire (608) and passed through the return or output wire (610). The additional wires (609, 611) are connected to high input impedance sense heads and have no current flow. Since the current is known, by relating the voltage in (Vin) and the voltage out (Vout), as total rope voltage (Vrope), and knowing the current in (iin), the resistivity of the rope (Rrope) can be determined.

$$Vrope=Vout-Vin$$

$$Rrope=Vrope/Vin$$

When the rope being tested reaches a predetermined threshold value of resistance, it is an indication to replace the rope. The threshold value can be determined by testing a similar rope at different stress levels for load and fatigue, for measured numbers of cycles, and measuring the corresponding resistance and residual load bearing strength. A relationship between resistance and load bearing capacity can then be established.

Because resistivity is affected by factors such as temperature and moisture, it is advantageous to use relative comparisons of individual cords in a multi-cord rope, or of multiple ropes, when applying the present invention. For instance, temperatures in a tall building can vary significantly between the top and bottom levels. By applying the present invention system to a rope having multiple cords of electrically conductive material, relative comparisons of resistivity with neighboring cords permits detection of changes in resistance despite effects from temperature, moisture or other environmental conditions.

Figure 10:
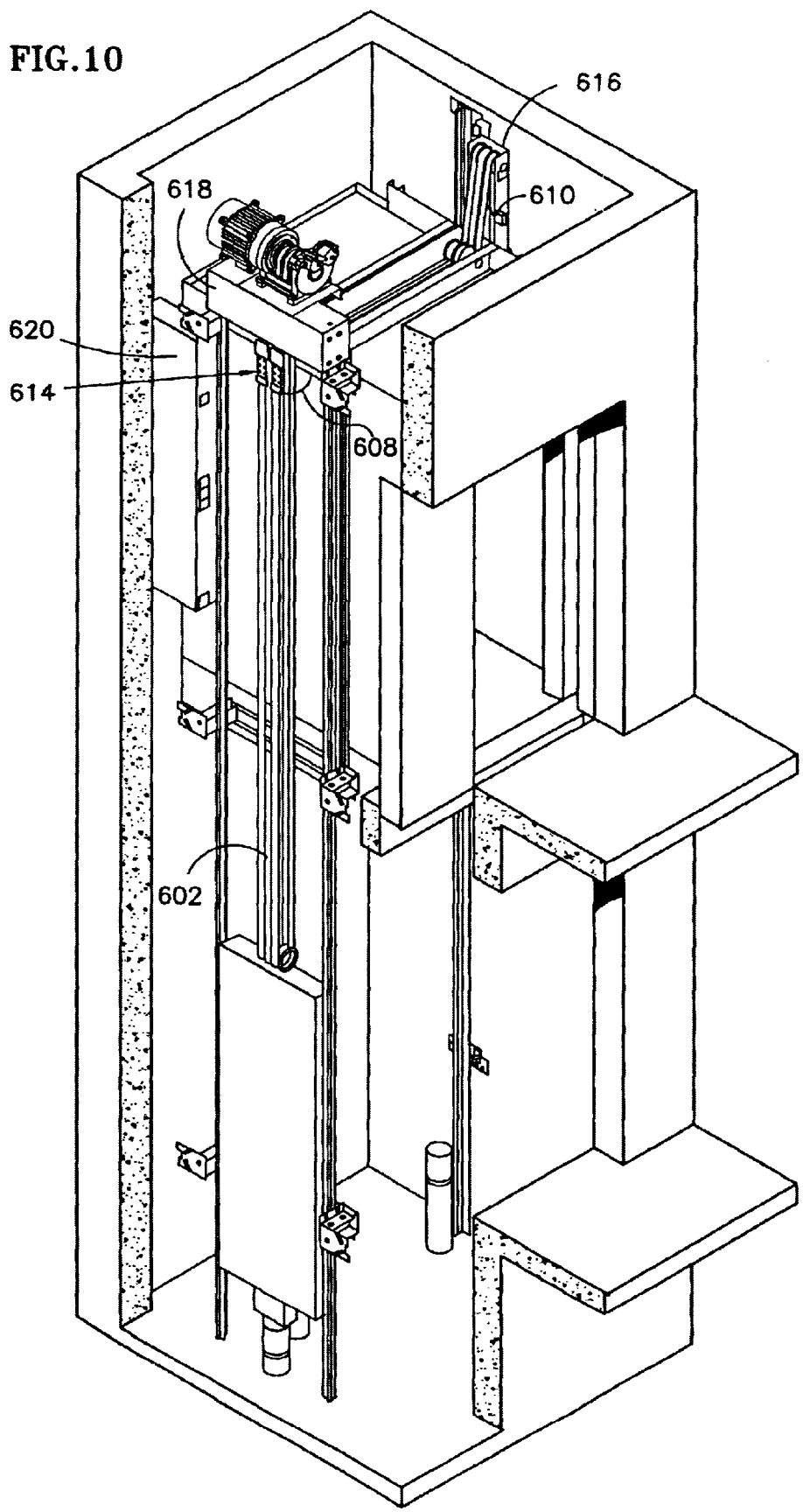
FIG. 10 is a partial, schematic view of a third embodiment apparatus according to the present invention mounted to an elevator system.

As shown in FIG. 10, current input and output leads (608, 610) can be made to an elevator rope (602) at termination points (614, 616) in an elevator system. A power source (618) and controller (620), shown schematically, may be connected via hardwire or other conventional means. The controller (620) may be programmed to correlate resistivity measurements with predetermined data indicative of tension-load bearing strength of the rope (602). A remote controller may be used through RF, modem connection or similar means for monitoring and controlling data input, current input, and readings.

CONCLUSION

The testing systems described in the foregoing may be implemented for continuous monitoring of rope condition, or they may be implemented periodically during maintenance procedures. The systems may be dedicated or portable systems.

While the preferred embodiments have been herein described, it is acknowledged and understood that various modifications may be made without departing from the scope of the presently claimed invention.

What is claimed is:

1. A method for approximating tension-load bearing capacity of a rope comprising a body of non-ferromagnetic insulator material in which a plurality of longitudinally extended ferromagnetic cord members is distributed transversely, the method comprising creating a partial magnetic circuit in a portion of the cord members by positioning a pair of magnetic poles adjacent to the body of the rope, wherein the poles are spaced longitudinally relative to the rope so that the partial magnetic circuit runs from one of the magnetic poles longitudinally through the portion of the cord members to the other of the magnetic poles;

measuring magnetic flux that is emanating from the cord members out through the body of the rope at a position between the poles along a longitudinal direction of the rope and is associated with the magnetic circuit; and comparing, based on the magnetic flux measured at the position between the poles, measured magnetic flux leakage to predetermined data indicative of tension-load bearing capacity.

2. An apparatus-for detecting degradation of a rope comprising a rope body of non-ferromagnetic insulator material encasing at least one longitudinally extended ferromagnetic component, the apparatus comprising:

a detector body comprising rope guide means for guiding the rope along the detector body;

a magnet fixed with respect to the body for creating a partial magnetic circuit in a portion of the ferromagnetic component of the rope that is adjacent to the detector body, the magnet comprising a pair of magnetic poles located adjacent the rope body and spaced longitudinally relative to the rope when the rope is guided along the detector body by the rope guide means so that the partial magnetic circuit runs from one of the magnetic poles longitudinally through the portion of the ferromagnetic component to the other of the magnetic poles;

magnetic flux sensing means mounted with respect to the detector body for monitoring magnetic flux that is emanating from the ferromagnetic component out through the rope body at a position between the poles and is associated with the magnetic field; and means for correlating the magnetic flux with rope degradation, wherein the at least one longitudinally extended ferromagnetic component comprises a plurality of ferromagnetic cord members, the magnetic flux sensing means comprises a plurality of magnetic flux sensors mounted to the body, the plurality of magnetic flux sensors each corresponds to one of the ferromagnetic cord members such that each magnetic flux sensor monitors the magnetic flux of a respective one of the cord members, and the plurality of magnetic flux sensors is positioned with respect to the detector body so that the magnetic flux sensors are on opposing sides of the rope when it is guided along the detector body.

3. An apparatus for detecting degradation of a rope comprising a rope body of non-ferromagnetic insulator material encasing at least one longitudinally extended ferromagnetic component, the apparatus comprising:

a detector body comprising rope guide means for guiding the rope along the detector body;

a magnet fixed with respect to the body for creating a partial magnetic circuit in a portion of the ferromagnetic component of the rope that is adjacent to the detector body, the magnet comprising a pair of magnetic poles located adjacent the rope body and spaced longitudinally relative to the rope when the rope is guided along the detector body by the rope guide means so that the partial magnetic circuit runs from one of the magnetic poles longitudinally through the portion of the ferromagnetic component to the other of the magnetic poles;

magnetic flux sensing means mounted with respect to the detector body for monitoring magnetic flux that is emanating from the ferromagnetic component out through the rope body at a position between the poles and is associated with the magnetic field;

means for correlating the magnetic flux with rope degradation; and means for mounting the apparatus in an elevator assembly in such a manner as to enable the rope guide means to engage and guide an installed elevator rope so that the apparatus can detect degradation of the elevator rope.

4. An apparatus for detecting degradation of a rope comprising a rope body of non-ferromagnetic insulator material encasing at least one longitudinally extended ferromagnetic component, the apparatus comprising a detector body comprising rope guide means for guiding the rope along the detector body;

a magnet fixed with respect to the body for creating a partial magnetic circuit in a portion of the ferromagnetic component of the rope that is adjacent to the detector body, the magnet comprising a pair of magnetic poles located adjacent the rope body and spaced longitudinally relative to the rope when the rope is guided along the detector body by the rope guide means so that the partial magnetic circuit runs from one of the magnetic poles longitudinally through the portion of the ferromagnetic component to the other of the magnetic poles;

magnetic flux sensing means mounted with respect to the detector body for monitoring magnetic flux that is emanating from the ferromagnetic component out through the rope body at a position between the poles and is associated with the magnetic field;

means for correlating the magnetic flux with rope degradation; and means for mounting the apparatus to an elevator hoist machine assembly in an elevator assembly in such a manner as to enable the rope guide means to engage and guide an installed elevator rope so that the apparatus can detect degradation of the elevator rope.

5. A monitoring system for monitoring the approximate load-bearing capacity of an elevator rope having a plurality of longitudinally-extended load-bearing elements that support the tension loads of the elevator system and a jacket that encompasses the load-bearing elements, said monitoring system comprising excitation means for exciting said load-bearing elements in a manner such that said jacket is not subject to excitation;

monitoring means for monitoring the level of excitation of each of said load-bearing elements; and correlation means for correlating the levels of excitation with the approximate load-bearing capacity of the elevator rope.

* * * * *

UNITED STATES PATENT AND TRADEMARK OFFICE
CERTIFICATE OF CORRECTION

PATENT NO.      : 6,633,159 B1
DATED           : October 14, 2003
INVENTOR(S)     : Robar et al.

It is certified that error appears in the above-identified patent and that said Letters Patent is hereby corrected as shown below:

<u>Title page,</u>
Item [75], Inventors, "Jack F. Gieras" should read -- Jacek F. Gieras --.

Signed and Sealed this

Sixteenth Day of December, 2003

JAMES E. ROGAN
*Director of the United States Patent and Trademark Office*